United States Patent
Karru et al.

(10) Patent No.: US 10,959,616 B2
(45) Date of Patent: Mar. 30, 2021

(54) ADAPTIVE NONINVASIVE BLOOD PRESSURE MONITORING SYSTEM AND METHOD

(71) Applicant: General Electric Company, Schenectady, NY (US)

(72) Inventors: Kristian Matti Karru, Kirkkonummi (FI); Otto Valtteri Pekander, Espoo (FI)

(73) Assignee: GENERAL ELECTRIC COMPANY, Schenectady, NY (US)

(*) Notice: Subject to any disclaimer, the term of this patent is extended or adjusted under 35 U.S.C. 154(b) by 308 days.

(21) Appl. No.: 14/830,857

(22) Filed: Aug. 20, 2015

(65) Prior Publication Data

US 2017/0049343 A1  Feb. 23, 2017

(51) Int. Cl.
*A61B 5/00* (2006.01)
*G06F 19/00* (2018.01)
*G16H 40/67* (2018.01)
*A61B 5/022* (2006.01)

(52) U.S. Cl.
CPC .......... *A61B 5/0022* (2013.01); *G06F 19/00* (2013.01); *G16H 40/67* (2018.01); *A61B 5/022* (2013.01); *A61B 5/02233* (2013.01); *A61B 5/7221* (2013.01); *A61B 5/7235* (2013.01); *A61B 5/742* (2013.01)

(58) Field of Classification Search
None
See application file for complete search history.

(56) References Cited

U.S. PATENT DOCUMENTS

| | | | |
|---|---|---|---|
| 4,974,597 A * | 12/1990 | Walloch | A61B 5/02208 600/493 |
| 6,405,076 B1 * | 6/2002 | Taylor | A61B 5/0205 128/901 |
| 8,211,030 B2 | 7/2012 | Donehoo et al. | |
| 2005/0033188 A1 * | 2/2005 | Whitaker | A61B 5/02233 600/490 |
| 2007/0055162 A1 * | 3/2007 | Vlahos | A61B 5/022 600/485 |
| 2009/0156946 A1 * | 6/2009 | Lane | A61B 5/022 600/490 |
| 2010/0125212 A1 * | 5/2010 | Kim | A61B 5/022 600/485 |
| 2012/0220884 A1 * | 8/2012 | Yamashita | A61B 5/022 600/490 |

(Continued)

FOREIGN PATENT DOCUMENTS

DE  3424535 A1 * 1/1986 ............. A61B 5/022
EP  0353315 A1 * 2/1990 ......... A61B 5/02116

OTHER PUBLICATIONS

U.S. Appl. No. 14/586,393, filed Dec. 30, 2014, "Common Display Unit for a Plurality of Cableless, Medical Sensors," Muuranto.

*Primary Examiner* — Christian Jang
*Assistant Examiner* — Sarah R Kingsley
(74) *Attorney, Agent, or Firm* — Andrus Intellectual Property Law, LLP

(57) ABSTRACT

A non-invasive blood pressure monitor has a blood pressure cuff and a wireless blood pressure determination unit. The wireless blood pressure determination unit automatically determines the fastest method for measuring blood pressure of a patient based on an initial blood pressure measurement made while inflating the cuff.

19 Claims, 5 Drawing Sheets

(56) References Cited

U.S. PATENT DOCUMENTS

| | | | |
|---|---|---|---|
| 2012/0289841 A1* | 11/2012 | Chen | A61B 5/022 600/490 |
| 2012/0330112 A1* | 12/2012 | Lamego | A61B 5/02225 600/301 |
| 2016/0100805 A1* | 4/2016 | Muehlsteff | A61B 5/02028 600/490 |

* cited by examiner

ADAPTIVE NONINVASIVE BLOOD PRESSURE MONITORING SYSTEM AND METHOD

BACKGROUND

The present disclosure generally relates to methods and systems for non-invasively measuring blood pressure. More specifically, the present disclosure relates to an automated non-invasive blood pressure (NIBP) monitor that automatically determines an optimal method for measuring blood pressure.

Automated blood pressure monitoring has rapidly become an accepted and central aspect of human health care. Such monitors are now a conventional part of patient monitoring, especially in emergency rooms, intensive and critical care units, and in the operating room. Traditionally, NIBP monitoring devices have been connected to sensors through cables and/or tubing. However, such cables and or tubing can be problematic because they inhibit patient movement and create obstacles to clinicians engaged in patient care. Thus, there has been a push towards wireless patient monitoring. However, the design of wireless monitoring devices presents challenges.

SUMMARY

A non-invasive blood pressure monitor has a blood pressure cuff and a wireless blood pressure determination unit. The wireless blood pressure determination unit automatically determines the fastest method for measuring blood pressure of a patient based on an initial blood pressure measurement made while inflating the cuff.

One embodiment of a method of measuring a blood pressure of a patient in a wireless, non-invasive blood pressure monitor includes inflating a blood pressure cuff of a wireless blood pressure monitor, and taking an initial blood pressure measurement during the inflation. It is then determined whether the initial blood pressure measurement meets an accuracy condition. A final blood pressure measurement is taken during deflation of the cuff if the initial blood pressure measurement does not meet the accuracy condition. However, if the initial blood pressure measurement does meet the accuracy condition, then the cuff is immediately deflated.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION OF THE DRAWINGS

Figure 1:
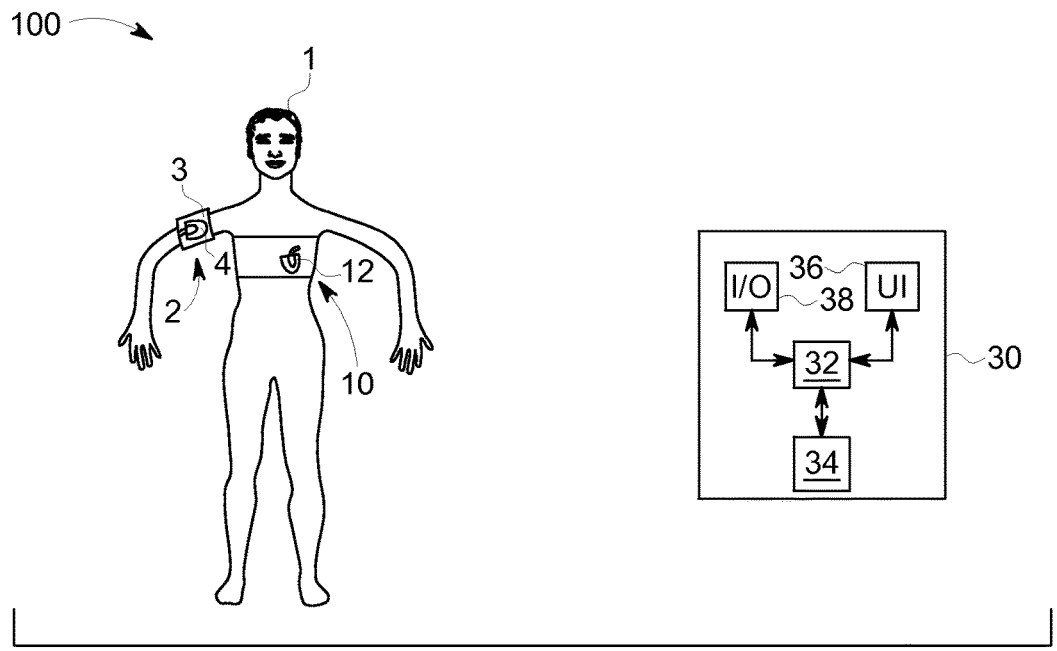
FIG. 1 is a block diagram of a patient monitoring environment including one embodiment of a wireless noninvasive blood pressure monitor.

FIG. 1 depicts one embodiment of a patient monitoring environment 100 wherein a patient 1 is being monitored using a wireless NIBP monitor 2 and a wireless ECG monitor 10. The wireless NIBP monitor 2 and the wireless ECG monitor 10 gather the respective physiological information from the patient without requiring a physical connection to a central monitoring device or power source. Thus, the wireless monitors 2 and 10 are self powered, such as by a battery contained therein, and may communicate physiological information of the patient, whether raw or processed physiological data, to another device or location via wireless means. In the embodiment depicted in FIG. 1, the wireless NIBP monitor 2 and the wireless ECG monitor 10 are in wireless communication with the central monitor 30. The wireless blood pressure monitor 2 has a blood pressure cuff 3 and a wireless blood pressure determination unit 4. The wireless ECG monitor 10 has an ECG sensor unit 11 (which may comprise one or more ECG sensors) and a wireless ECG determination unit 12. The central monitor 30 has wireless transceiver 38 that communicates with the wireless transceivers of patient monitoring devices, including transceivers in wireless NIBP monitor 2 and in the wireless ECG monitor 10. Thus, the wireless transceiver 38 communicates information between the patient monitors 2 and 10 and the processing unit 32 of the central monitor 30. The wireless transceiver 38 of the monitor 30 may communicate with wireless transceivers of the respective monitoring devices 2 and 10 by any wireless means, such as via a network operating on the medical body area network (MBAN), body area network (BAN), wireless medical telemetry service (WMTS) the spectrum or on a Wi-Fi-compliant local area network (WLAN), or by Bluetooth or another wireless communication standard.

The central monitor 30 may also have a user interface 36. The user interface 36 may provide a means through which a clinician may receive or view information from the patient monitors 2 and 10 and/or to provide input to the patient monitors 2 and 10. The processing unit 32 may also be connected to a digital storage device 34 for storing the physiological data collected by the various sensor devices 2 and 10. The digital storage device 34 may also store processed physiological data and/or other information generated by the processor 32, and/or may operate to store other relevant patient information.

Figure 2:
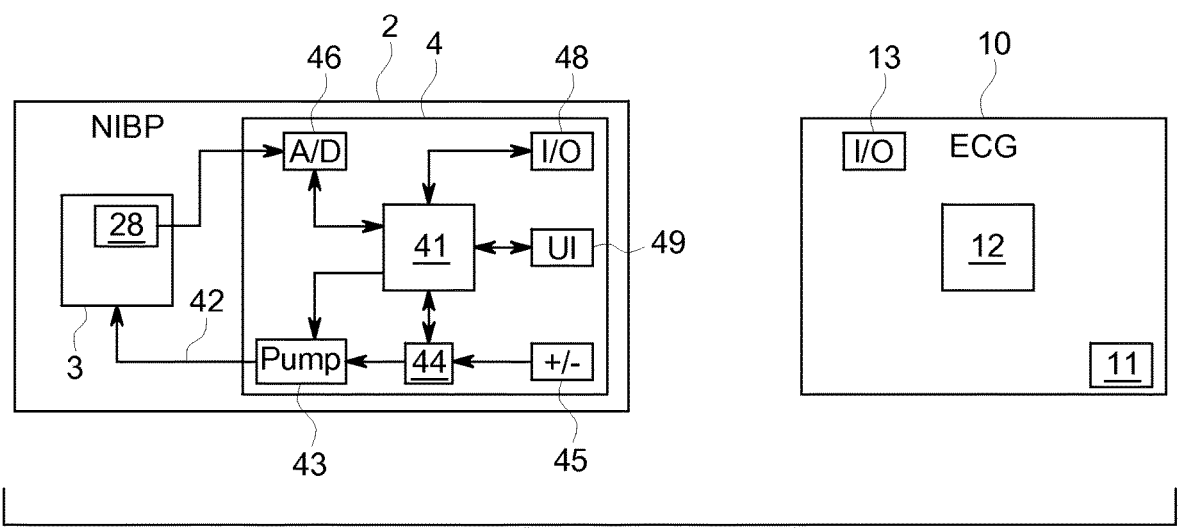
FIG. 2 is a block diagram of a wireless noninvasive blood pressure monitor and a wireless ECG monitor.

In the embodiment of FIG. 1, each wireless monitoring device 2 and 10 communicates with the central monitor 30. Thus, any communication of information between the wireless monitoring devices 2 and 10 goes through the central monitor 30. However, in the embodiment of FIG. 2, the wireless NIBP monitor 2 and the wireless ECG monitor 10 may communicate directly with one another, including communicating information about the patient status, or other monitoring information. Specifically, the wireless noninvasive blood pressure monitor 2 has a wireless transceiver 48 responsible for receiving input information and transmitting output information. Likewise, the wireless noninvasive ECG monitor 10 has a wireless transceiver 13 responsible for receiving input information and transmitting output information. For example, the wireless transceiver 48 of the wireless NIBP monitor 2 may communicate with the wireless transceiver 13 of the wireless ECG monitor 10 to receive ECG information of the patient 1. As described above with respect to the embodiment of FIG. 1, the wireless transceivers 48 and 13 may communicate by any wireless communication standards known in the art, including MBAN, BAN, WMTS, Wi-Fi, Bluetooth, or the like.

Figure 3:
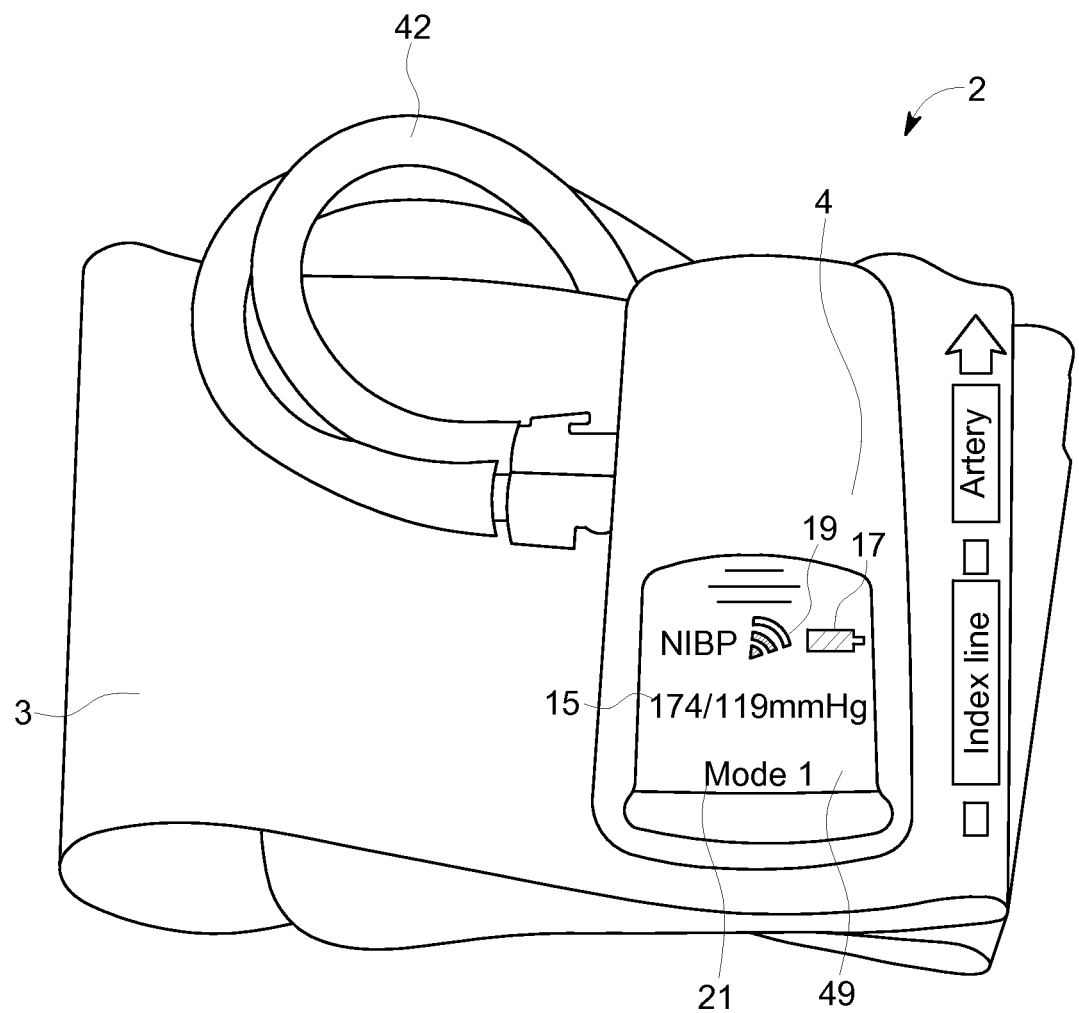
FIG. 3 depicts an exemplary embodiment of a wireless noninvasive blood pressure monitor.

The wireless NIBP monitor 2 has a blood pressure cuff 3 and a wireless blood pressure determination unit 4. As depicted in FIG. 3, the blood pressure determination unit 4 may be physically connected to the cuff 3 so that the wireless NIBP monitor 2 can easily be worn by the patient 1, such as by wrapping the cuff around the patient's arm or leg in a manner known in the art. The blood pressure determination unit 4 is configured to inflate the blood pressure cuff 3 on the patient, and to then determine a blood pressure of the patient according to the methods described herein. The blood pressure determination unit 4 may have a display 49 that displays, for example, the patient's blood pressure 15 measured according to the methods disclosed herein, a battery status 17, and or a wireless connectivity status 19. The display 49 may also provide a mode indicator 21 which may indicate the mode, or method, used to calculate the patient's blood pressure 15. For example, the mode indicator 21 may indicate whether the blood pressure value for the patient was measured during continuous inflation of the cuff 3, stepwise inflation of the cuff 3, or stepwise deflation of the cuff 3.

Referring again to FIG. 2, the blood pressure determination unit 4 has a pump 43 configured to inflate the blood pressure cuff 3. The pump 43 pumps air into the cuff 3 via one or more pump lines 42. The pump 43 is powered by battery 45, also housed in the blood pressure determination unit 4. The battery 45 is connected to the pump 43 through power gauge and protection module 44, which regulates the power distribution within the blood pressure determination unit 4. For example, the power from the battery 45 may be distributed via the power gauge and protection module 44 to the processor 41, analog to digital convertor 46, wireless transmitter 38, user interface 49, and pump 43. The battery 45 may be any battery capable of providing sufficient power, and is preferably a rechargeable battery. The user interface 49 may be a display, such as shown in FIG. 3. Additionally, the user interface 49 may enable user input, such as to select a mode or to initiate a blood pressure measurement.

The wireless NIBP monitor 2 measures the patient's blood pressure by inflating the cuff 3 around the patient's arm and measuring the pressure changes in the cuff via pressure sensor 28 to measure pressure oscillations caused by blood flow in the patient's arm. Specifically, the processor 41 causes the pump 43 to inflate the cuff 3 via pump line 42. The processor 41 controls the pressure in the cuff 3 according to the methods disclosed herein to facilitate and optimize blood pressure measurement. Pressure measurements sensed by the pressure sensor 28 are transmitted to the analog-to-digital converter (A/D converter) 46, which digitizes the signals and transmits them to the processor 41. The A/D converter 46 may be any device or logic set capable of digitizing analog physiological signals. For example, the A/D converter 46 may be an analog front end (AFE).

Through the experimentation and research in the relevant field, the present inventors have recognized that certain design challenges and difficulties exist in creating a wireless blood pressure monitor that is small enough and light enough for a patient to wear comfortably. For example, pump devices incorporated in presently available wired blood pressure monitors are bulky, heavy, and energy intensive. Such pumps cannot be adequately powered by a small battery ideal for incorporation in a wireless NIBP monitor 2. Such pumps are also loud and thus not well suited for a wireless monitoring situation where the entire NIBP monitor 2 is located on the patient, likely on a patient's upper arm and thus close to the patient's ear. Moreover, the inventors have also recognized that smaller pumps that are quieter and less power intensive take longer to inflate the cuff 3, which increases the amount of time that the patient must experience discomfort during the standard blood pressure measurement.

Accordingly, the present inventors developed the disclosed system and method that determines and executes the fastest method of obtaining a blood pressure measurement from the patient 1 while still maintaining one or more accuracy conditions. The present method also minimizes the pressure to which the cuff has to be inflated in order to obtain an accurate blood pressure measurement. The goal is to minimize the amount of time that the cuff 3 is inflated, thereby minimizing patient discomfort. Additionally, minimizing the inflation pressure and the inflation time minimizes the amount of power utilized for each measurement cycle, thereby increasing battery life for the device.

The processor 41 of the blood pressure determination unit 4 determines and executes the fastest method of obtaining a non-invasive blood pressure measurement from a patient 1 by using the inflation cycle to measure the patient's blood pressure and/or obtain information that can expedite the measurement process on the deflation cycle, thereby minimizing the amount of time that the blood pressure cuff needs to remain inflated. This differs from typical, presently available NIBP monitoring devices, which inflate to a predetermined target inflation pressure and then measure the patient's blood pressure as the cuff is deflated in a series of pressure steps. This presently available method works fine for wired NIBP monitors because they have larger pumps that quickly reach a target pressure. However, the inflation time is much longer with the smaller pumps 43 that are well suited for wireless monitoring applications, and thus the standard blood pressure measurement methods utilized in presently available, wired NIBP monitors is undesirable.

Figure 4A:
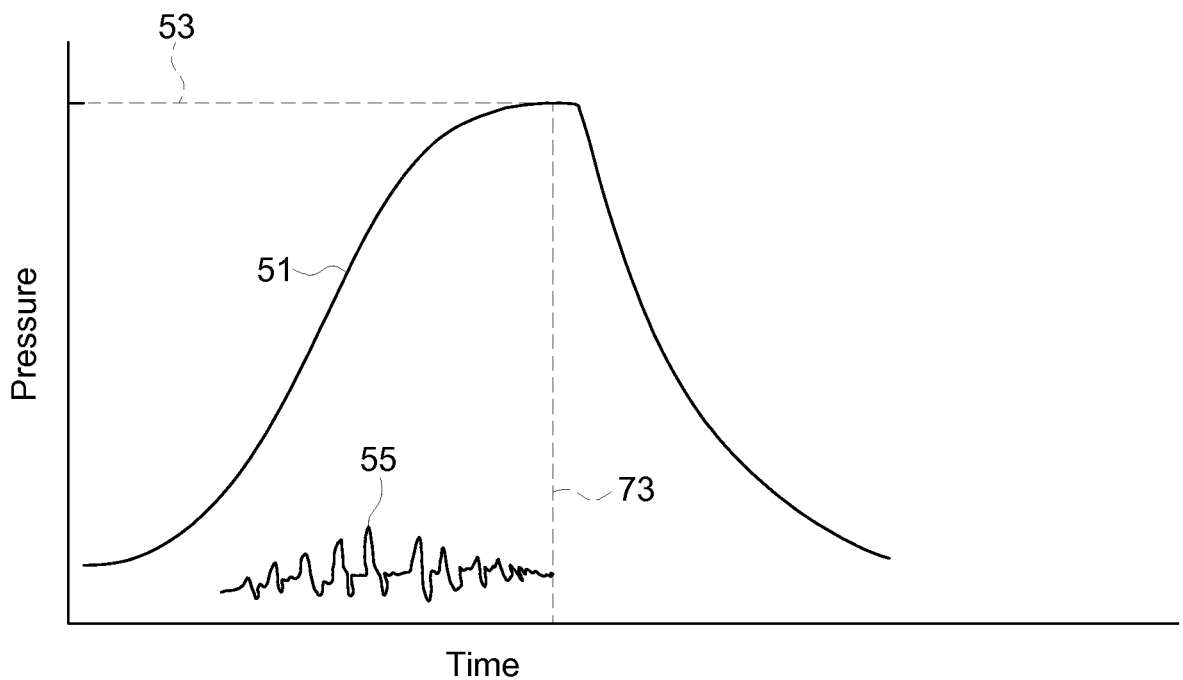
FIG. 4a depicts an exemplary method of measuring blood pressure of a patient according to the present disclosure.

The present inventors realized that the longer inflation time with the smaller pump 43 can be used advantageously to take an initial blood pressure measurement, including an estimated systolic and/or diastolic pressure, and/or to determine when the maximum required inflation pressure has been reached. FIG. 4A provides a graphical depiction of a first method of measuring blood pressure that yields calculation of an initial blood pressure measurement during continuous inflation of the cuff 3. In FIG. 4A, the cuff pressure profile 51 shows that the pressure in the cuff 3 increases over a relatively long period of time, reaching a maximum required pressure 53 at an inflation time 73. As will be known to one of skill in the art, the maximum required pressure 53 is typically that pressure at which the blood pressure cuff 3 fully occludes blood flow through the surface arteries under the cuff 3. Typically, the blood pressure cuff 3 is placed around the patient's upper arm over the brachial artery. The blood pressure cuff 3 is inflated to the maximum required pressure 53 that fully occludes the brachial artery, i.e., prevents blood from flowing through the brachial artery at any time in the heart cycle. Oscillations in the cuff pressure 55 are measured during the inflation, such as via pressure sensor 28. As the pressure in the cuff 3 reaches the maximum required pressure 53, the cuff pressure oscillations 55 become smaller. When the cuff pressure oscillations disappear, the brachial artery has been occluded (if cuff 3 is placed on the upper arm) and the maximum required pressure 53 has been reached. The cuff pressure oscillations 55 measured during inflation of the cuff 3 may be utilized to determine an initial blood pressure, including an initial systolic pressure, an initial diastolic pressure, and/or an initial mean arterial pressure (MAP).

Figure 4B:
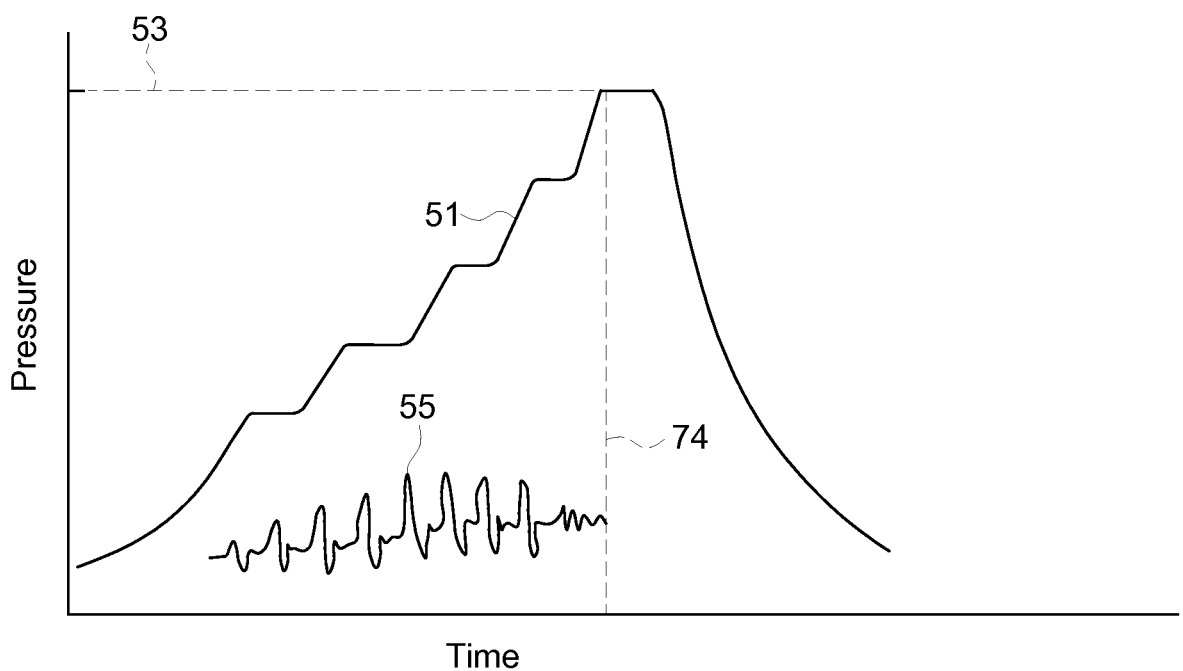
FIG. 4b depicts another exemplary method of measuring blood pressure of a patient according to the present disclosure.

FIG. 4B depicts a second method of calculating a blood pressure during inflation of the cuff 3. In FIG. 4B, the cuff pressure profile 51 is increased in a stepwise manner, through a series of inflation steps, until the maximum required pressure 53 is reached. The stepwise inflation of the cuff 3 takes longer than the continuous inflation, and thus the inflation time 74 of the second method is longer than the inflation time 73 of the first method depicted in FIG. 4A. Although various values for each pressure step can be utilized, in an exemplary example, each pressure step may be about 8 mmHG per step. However, the pressure step may be varied based on the expected blood pressure values. As described above, the cuff pressure oscillations 55 are monitored during the inflation of the cuff 3 to determine the maximum required pressure 53 and to calculate an initial blood pressure for the patient, preferably including an initial systolic pressure and an initial diastolic pressure.

Figure 4C:
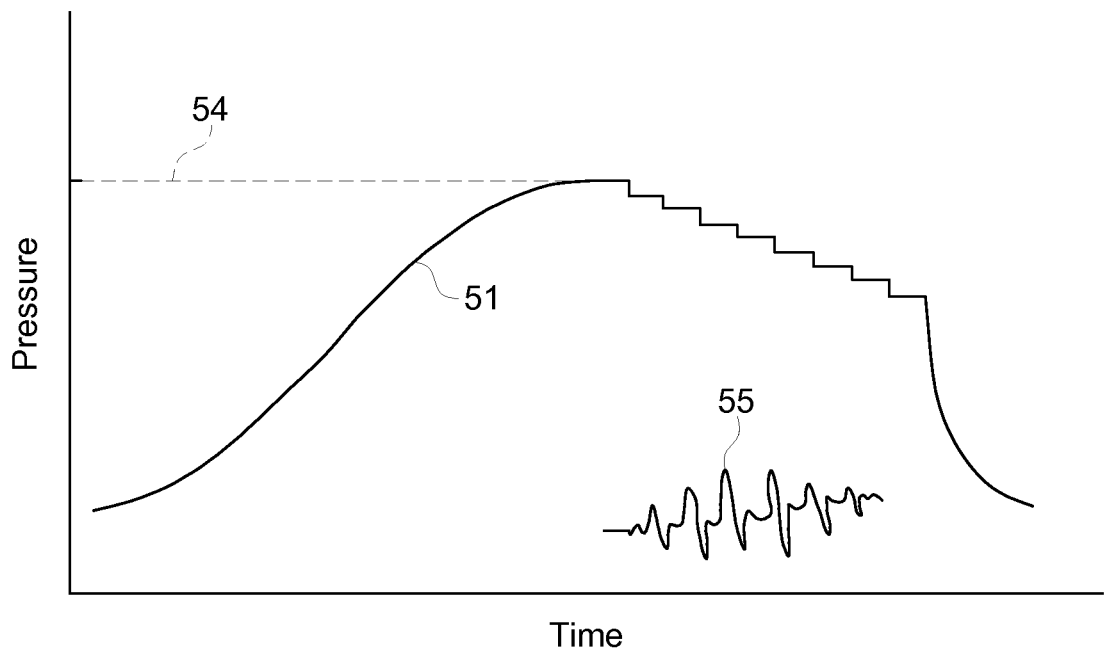
FIG. 4c depicts another exemplary embodiment of a method of measuring a blood pressure of the patient according to the present disclosure.

FIG. 4C depicts a third and most common method of calculating blood pressure for a patient, where the pressure is measured during deflation of the cuff 3. The cuff pressure profile 51 is increased to a target inflation pressure 54, and then is decreased in a series of deflation steps, or stepwise deflation. As will be known to one of skill in the art, several methods are known for calculating target inflation pressure 54. For example, the target inflation pressure 54 may be calculated based on previous cuff pressure profiles 51 and/or blood pressure measurements taken for the patient. Alternatively or additionally, the target inflation pressure 54 may be based on patient demographic data and our other information related to the health of the patient. The patient's blood pressure is calculated based on the cuff pressure oscillations 55 measured during the stepwise deflation.

Figure 5:
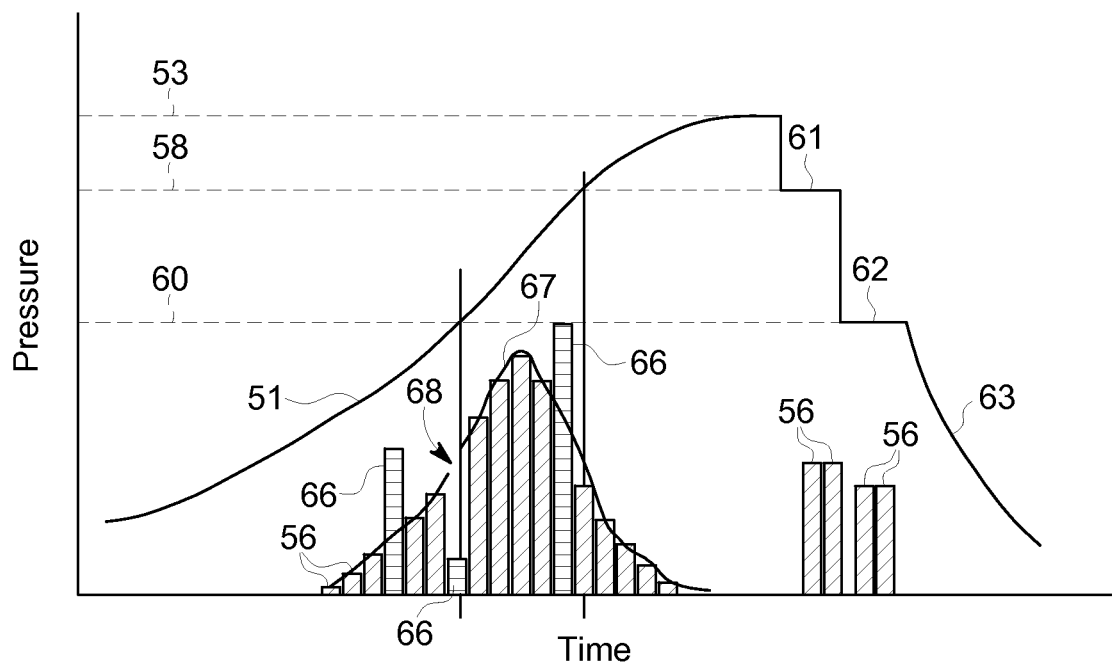
FIG. 5 depicts another exemplary embodiment of a method of measuring a blood pressure of a patient according to the present disclosure.
Figure 6:
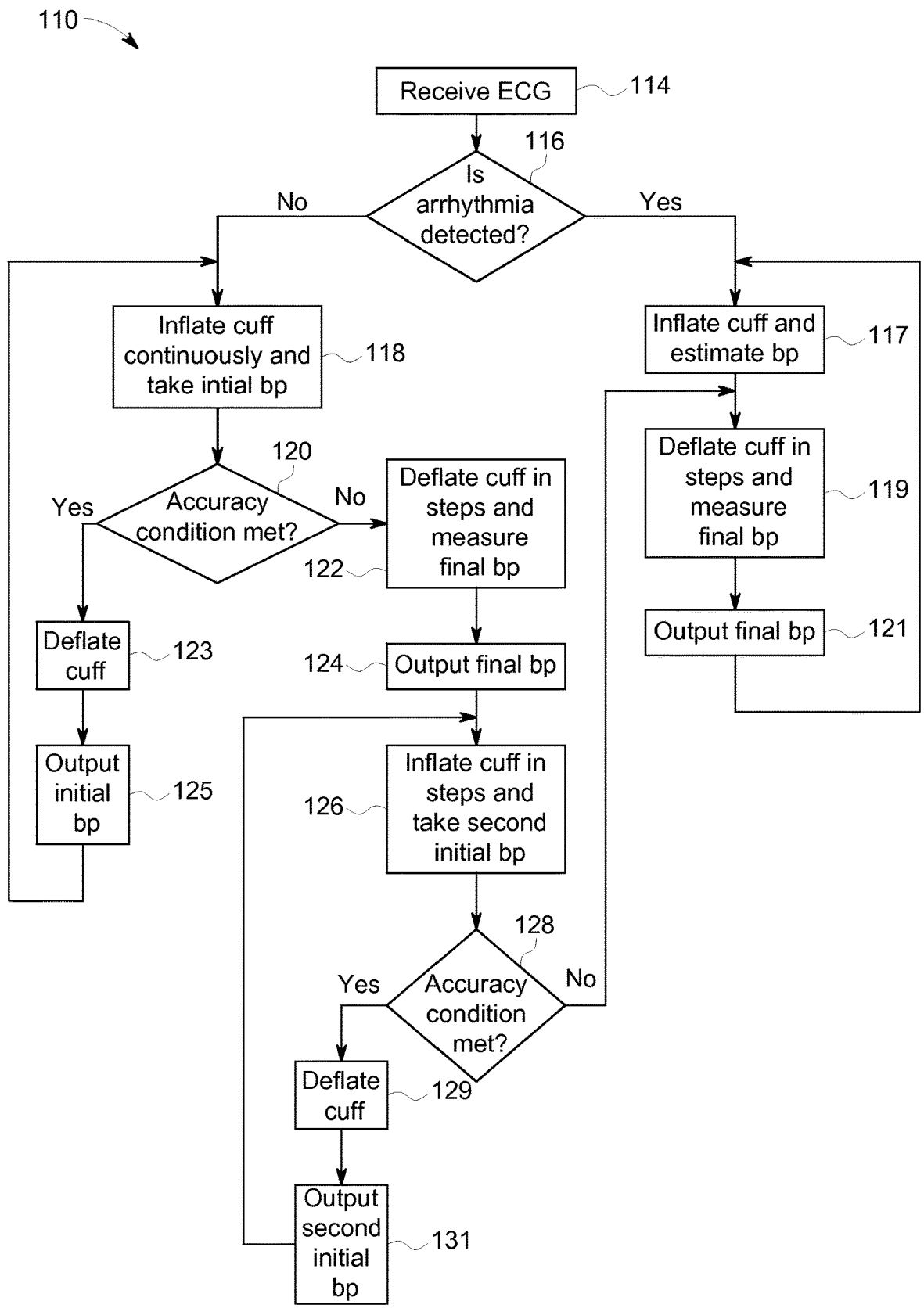
FIG. 6 is a flow chart depicting another embodiment of a method of measuring blood pressure of a patient according to the present disclosure.

The method depicted in FIG. 4C may be used in conjunction with either of the inflation measurement methods depicted in FIG. 4A or 4B. In such an embodiment, the target inflation pressure 54 may be the maximum acquired pressure 53 as described above. FIG. 5 demonstrates an exemplary embodiment of a method of measuring blood pressure of the patient including measurement during the inflation and deflation periods of the cuff pressure profile 51. As will be known to one of skill in the art, cuff pressure oscillation amplitudes 56 may be determined from the cuff pressure oscillations 55 recorded during the inflation and/or deflation of the blood pressure cuff 3. The processor 41 within the blood pressure determination unit 4 can then calculate the systolic pressure 58 and the diastolic pressure 60. Specifically, as the measurement cycles progress, the pressure oscillation amplitudes 56, or peak amplitudes of the oscillation pulses, generally become larger to a maximum and then become smaller as the cuff pressure continues toward the target inflation pressure 54 or deflation, whichever is applicable. Specifically, on inflation the pressure oscillation amplitudes 56 initially increase to a maximum as the arterial flow is slightly occluded, and then decrease to zero as the arterial space becomes completely occluded. Likewise, during deflation, the pressure the pressure oscillation amplitudes 56 seen in the cuff 3 will increase to a maximum as the arterial space partially re-opens, and then decrease as the cuff 3 is deflated.

The general pattern of pressure oscillation amplitude during inflation and deflation is illustrated by line 66 in FIG. 5. In FIG. 5, the cuff pressure profile 51 increases over a relatively long period, such as may be performed by a pump 43 in a wireless NIBP monitor, and then decreased in a stepwise manner. The pressure oscillation amplitudes 56 and the corresponding cuff pressure values from the cuff pressure profile 51 are used by the processor 41 to calculate the an initial blood pressure for the patient during inflation of the cuff 3, including the systolic pressure 58 and/or diastolic pressure 60. If the initial pressure measurement meets the required accuracy conditions, then the processor 41 can output the initial pressure measurement as the blood pressure measurement for the patient and can immediately deflate the cuff 3, as is depicted in the cuff pressure profile 51 of FIG. 4a. Thereby, the duration for which the cuff 3 was inflated is minimized. However, if the accuracy condition is not met, then that initial pressure may be used to strategically deflate the cuff 3 and obtain a final pressure measurement more quickly during deflation.

The processing unit 41 determines whether the initial blood pressure measurement meets one or more accuracy conditions. For example, the accuracy condition may require that the initial blood pressure measurement be within a predetermined range of a previous blood pressure measurement for the patient. The previous blood pressure measurement may be a stored value that represents a "normal" for the patient. Alternatively or additionally, the previous blood pressure measurement may be a previous value measured by the blood pressure determination unit 4 at an earlier time. In still other embodiments, the previous blood pressure measurement may be an average or mean of blood pressure values previously obtained from the patient.

Alternatively or additionally, the processor 41 may receive medical condition information for the patient, and may rely on such information to determine whether the initial blood pressure measurement is accurate and reliable. For example, the processor may base the accuracy assessment on information received from the wireless ECG monitor 10 about the patient's heart rate or heart beat. For example, if the wireless ECG monitor 10 indicates that the patient is experiencing cardiac arrhythmia, the processor 41 may determine that the initial blood pressure measurement does not meet the accuracy condition. In another example, if the patient heart beat is naturally very slow (which might be the case, for example, on professional cyclists), the device may not be able to collect enough samples within the inflation period 51, and thus the predetermined accuracy condition is not met. For example, the slow heart rate may be detected by the ECG monitor 10 or from a pulse oximeter. In that instance, the device may only try to detect the right target inflation pressure 54 and estimate where to stop pumping. Thereafter, the operation mode shown in FIG. 4C may be used to determine an accurate blood pressure of the patient. In still other embodiments, the accuracy condition may include assessment of noise or artifact, such as due to movement of the patient or physical interference with the cuff. If the patient is moving a lot, for example a baby, the data obtained during the inflation period is not likely to be consistent and a targeted step down process may be needed to verify the blood pressure measurement. An exemplary instance of this scenario is shown at FIG. 5 and described below.

In situations where the initial blood pressure measurement taken during inflation does not meet an accuracy condition, the final blood pressure may be taken during deflation of the blood pressure cuff, as is exemplified in FIG. 4c and also in FIG. 5. In that instance, the processor 41 of the blood pressure determination unit 4 may utilize any information it gains from measurements during inflation of the cuff 3 to minimize the cuff inflation and patient discomfort, and to inform and adjust the measurement process of the final blood pressure taken during the deflation stage. First, the wireless NIBP monitor 2 may use the cuff pressure oscillation measurements 55 during inflation period 51 to determine the maximum required pressure 53. As such, the cuff 3 will not be inflated beyond the maximum required pressure 53. Further, the processor 41 may utilize the cuff pressure oscillation 55 and/or the pressure oscillation amplitude 56 to provide information about the patient's blood pressure, such as an estimate of the patient's current systolic pressure 58 and/or diastolic pressure 60, and to strategically deflate the cuff 3 to minimize the number of deflation steps necessary to obtain a final blood pressure during deflation of the cuff 3. For example, the initial pressure measurement may be utilized as a systolic pressure estimate 58 and/or a diastolic pressure estimate 60. Those initial values may be used to deflate the blood pressure cuff 3 to the point where the relevant pressure oscillation amplitudes 56 can be measured to calculate a final systolic pressure and diastolic pressure. Thereby, the final blood pressure measurement can be made quickly using fewer, targeted deflation steps that are the most likely to yield results quickly. However, in other embodiments, the cuff 3 may be deflated in a more conventional manner, such as is depicted in FIG. 4C, using multiple smaller steps. Although various values for each pressure step can be utilized, in an exemplary instance, each pressure step may be decreased by about 8 mmHG per step.

In the example of FIG. 5, the cuff 3 is deflated in three steps based on the initial blood pressure measurement, including the initial systolic pressure estimate 58 and initial diastolic pressure estimate 60 measured or estimated during inflation of the cuff. Specifically, the first deflation step 61 deflates the cuff 3 to a pressure where a final systolic pressure is likely to be measurable based on the initial blood pressure measurements made during the inflation phase. Likewise, the second step 62 deflates the cuff 3 to a pressure where a final diastolic pressure is likely to be measurable based on the initial measurements performed during the inflation phase. Finally, in a third step 63, the pressure in the cuff is completely released.

In a situation where one or more measured pressure values do not meet an accuracy condition due to noise or artifacts, for example the patient moves, the single point or points that do not meet the predetermined accuracy condition might be verified by visiting those spots during the step down. For example, if there is one spot in pressure curve that doesn't seem to make sense, the system may visit that spot to see if that data was only noise. If consistent data is obtained at that point, then the blood pressure may be successfully estimated with only one step down. FIG. 5 provides one example of where an initial blood pressure measurement does not meet a predetermined accuracy condition due to artifact 66 in the pressure oscillation amplitude measurements 56. Specifically, artifact 66 interferes with the initial blood pressure measurement such that the pressure data 68 on the estimated pressure curve 67 near the initial diastolic pressure estimate 60 does not meet the predetermined accuracy condition. Additionally, due to the level of artifact 66 present in the pressure oscillation amplitude measurements 56, the system may determine that the initial systolic pressure estimate 58 also does not meet the predetermined accuracy condition. Thus, the cuff is deflated in three steps 61-63 as described above to verify the estimated values and obtain final systolic and diastolic pressure measurements.

Following the determination of the final blood pressure value during deflation of the cuff 3, the processor may perform a different measurement technique to see if it can get an accurate initial blood pressure measurement during the next inflation of the cuff 3. Specifically, the processor 41 may utilize a stepwise inflation method, such as that depicted in FIG. 4b. Thus, the cuff 3 may be inflated in a stepwise manner, pausing at predetermined increments to get clearer measurements of the cuff pressure oscillation 55 and the pressure oscillation amplitudes 56. If this second initial blood pressure measurement measured during the second inflation step meets the required accuracy conditions, then the cuff may be immediately deflated. The blood pressure determination unit 4 may then use the stepwise inflation method going forward to measure the blood pressure of the patient. Accordingly, this second method depicted in FIG. 4B of measuring blood pressure during the stepwise inflation still minimizes the amount of time that the cuff 3 has to be inflated in order to obtain the blood pressure measurement. While not as quick as the first measurement method measuring the pressure during continuous inflation of the cuff (FIG. 4A), the second method still minimizes inflation time and inflation pressure by completing the blood pressure measurement on the inflation phase and allowing for immediate deflation of the cuff 3.

However, if the second initial blood pressure measurement does not meet the required accuracy conditions, the blood pressure determination unit 4 will measure a second final blood pressure during a stepwise deflation of the cuff, as is described above and depicted in FIG. 4c and/or FIG. 5. Going forward then, the blood pressure determination unit 4 may revert back to continuous inflation of the cuff 3, and then taking a final blood pressure measurement during deflation. Thereby, the blood pressure determination unit 4 executes the fastest method that achieves an accurate blood pressure measurement. The blood pressure determination unit 4 may continue to measure the cuff pressure oscillations 55 during inflation, such as is depicted and discussed with respect to FIG. 5. In other embodiments, the blood pressure determination unit 4 may only measure the blood pressure during deflation of the cuff 3, such as is depicted in FIG. 4c.

A method 110 of measuring blood pressure includes receiving ECG data at step 114. At step 116, the ECG data is analyzed to determine whether an arrhythmia is detected. Such an arrhythmia detection may be performed, for example, by an ECG monitor 10 or a central monitor 30 and may be transmitted to the wireless NIBP monitor 2. Alternatively, the processor 41 of the wireless NIBP monitor 2 may receive cardiac data and may assess the data to determine whether an arrhythmia is present. If an arrhythmia is present, the wireless blood pressure determination unit 4 inflates the cuff at step 117 in a continuous manner and estimates blood pressure during the inflation step. At step 119, the cuff is deflated in a stepwise manner and a final blood pressure is measured. The deflation steps may be performed based on the initial blood pressure estimate measured at step 117, such as is depicted and described with respect to FIG. 5. In an alternative embodiment, the cuff could be inflated without performing any estimation or initial measurement, and the final blood pressure could be measured in a standard stepwise deflation as is exemplified by FIG. 4C. A final blood pressure is then output at step 121. Going forward, the blood pressure determination unit 4 may continue measuring the patient's blood pressure according to the method steps 117, 119, 121.

If an arrhythmia is not detected at step 116, then the blood pressure determination unit 4 continues to step 118 where it inflates the cuff continuously and takes an initial blood pressure during that continuous inflation. At step 120, the blood pressure determination unit 4 assesses whether the initial blood pressure measurement meets an accuracy condition. If the accuracy condition is met, then the initial blood pressure is reliable and usable and the blood pressure determination unit 4 does not need to continue the measurement process. Thus, the cuff is immediately deflated at step 123 where the pressure is released from the cuff. The initial blood pressure is outputted at step 125 as the blood pressure measurement for the patient. On the next measurement cycle, the blood pressure determination unit 4 will return to step 118 where it will take the initial blood pressure measurement during continuous inflation of the cuff.

If, at any point, the accuracy condition is not met at step 120, then the blood pressure determination unit 4 continues to step 122 where it deflates the cuff in steps and measures a final blood pressure. The final blood pressure is outputted at step 124 as the blood pressure for the patient. Then, on the next measurement cycle, the blood pressure determination unit 4 inflates the cuff in steps and attempts to take a second initial blood pressure measurement. At step 128, the blood pressure determination unit 4 assesses whether the second initial blood pressure meets the accuracy condition. If so, the measurement process is over and the pressure in the cuff is immediately released at step 129. The second initial blood pressure is then outputted as the patient's blood pressure measurement at step 131. The blood pressure determination unit 4 may then return to step 126 to make the next blood pressure measurement for the patient according to the steps of 126, 128, 129, and 131.

If, on the other hand, the second initial blood pressure measurement does not meet the accuracy condition at step 128, then the blood pressure determination unit 4 may continue to step 119, where a final blood pressure measurement is made. The blood pressure determination unit 4 may then determine that initial blood pressure measurements made during the inflation phase are not sufficiently accurate and thus a final blood pressure measurement is required according to the steps 117, 119, and 121.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:
1. A noninvasive blood pressure monitor comprising:
   a blood pressure cuff inflatable to measure a blood pressure;
   a wireless blood pressure determination unit configured to:
   continuously inflate the blood pressure cuff;
   receive pressure measurements from a pressure sensor in the blood pressure cuff during continuous inflation;
   determine an initial blood pressure measurement based on the pressure measurements taken during continuous inflation according to a continuous inflation measurement method;
   automatically select, based on an accuracy of the initial blood pressure measurement, a method for measuring blood pressure of a patient between the continuous inflation measurement method, a stepwise inflation measurement method, and a stepwise deflation measurement method including by:
   determining if the initial blood pressure measurement meets an accuracy condition; and
   if the initial blood pressure measurement meets the accuracy condition, continuing a future blood pressure measurement cycle according to the continuous inflation measurement method;
   if the initial blood pressure measurement does not meet the accuracy condition, selecting a second method for measuring blood pressure for the future blood pressure measurement cycle, wherein the second method is selected from one of the stepwise inflation measurement method and the stepwise deflation measurement method.

2. The noninvasive blood pressure monitor of claim 1, wherein the wireless blood pressure determination unit takes a final blood pressure measurement during deflation of the blood pressure cuff if the initial blood pressure measurement does not meet an accuracy condition.

3. The noninvasive blood pressure monitor of claim 2, wherein the accuracy condition includes a comparison between the initial blood pressure measurement and a previous blood pressure measurement to determine whether the initial blood pressure measurement is within a predetermined range of the previous blood pressure measurement.

4. The noninvasive blood pressure monitor of claim 2, wherein the wireless blood pressure determination unit further determines that the initial blood pressure measurement does not meet the accuracy condition, and then takes a second initial blood pressure measurement during a subsequent blood pressure measurement cycle using the stepwise inflation measurement method.

5. The noninvasive blood pressure monitor of claim 2, wherein the wireless blood pressure determination unit takes the final blood pressure measurement by deflating the blood pressure cuff in steps, wherein the pressure value of one or more of the steps is based on the initial blood pressure measurement.

6. The noninvasive blood pressure monitor of claim 1, wherein the wireless blood pressure determination unit automatically selects the method for measuring blood pressure based further on medical condition information of the patient, including at least one of an arrhythmia and a slow heart rate.

7. The noninvasive blood pressure monitor of claim 6, wherein the wireless blood pressure determination unit receives the medical condition information from one of an electrocardiograph or a pulse oximeter.

8. The noninvasive blood pressure monitor of claim 7, wherein the wireless blood pressure determination unit takes a final blood pressure measurement during deflation of the blood pressure cuff if the medical condition information from the electrocardiograph indicates a cardiac arrhythmia.

9. The noninvasive blood pressure monitor of claim 1, wherein the wireless blood pressure determination unit takes a second initial blood pressure measurement during a subsequent blood pressure measurement cycle using the stepwise inflation measurement method if the initial blood pressure measurement during the continuous inflation of the blood pressure cuff does not meet the accuracy condition.

10. A method of measuring a blood pressure of a patient in a wireless non-invasive blood pressure monitor, the method comprising:
   continuously inflating a blood pressure cuff of a wireless blood pressure monitor;
   measuring pressure changes in the blood pressure cuff with a pressure sensor during the continuous inflation of the blood pressure cuff;
   determining an initial blood pressure measurement of a patient based on the measured pressure changes;
   determining if the initial blood pressure measurement meets an accuracy condition;
   if the initial blood pressure measurement meets the accuracy condition, immediately deflating the blood pressure cuff and selecting a continuous inflation measurement method for measuring blood pressure for the patient;
   if the initial blood pressure measurement does not meet the accuracy condition:
   stepwise deflating the blood pressure cuff;
   determining a final blood pressure measurement based on pressure changes in the blood pressure cuff measured by the pressure sensor during the stepwise deflation;
   stepwise inflating the blood pressure cuff;
   determining a second initial blood pressure measurement of the patient based on pressure changes in the blood pressure cuff measured by the pressure sensor during the stepwise inflation;
   determining if the second initial blood pressure measurement meets the accuracy condition;
   if the second initial blood pressure measurement meets the accuracy condition, immediately deflating the blood pressure cuff and selecting a stepwise inflation measurement method for measuring blood pressure for the patient;
   if the second initial blood pressure measurement does not meet the accuracy condition, selecting a stepwise deflation measurement method for measuring blood pressure for the patient; and
   continuing inflation and deflation of the blood pressure cuff in future blood pressure measurements according to the selected method for measuring the blood pressure for the patient.

11. The method of claim 10, wherein the step of determining if the initial blood pressure measurement meets the accuracy condition includes comparing the initial blood pressure measurement with a previous blood pressure measurement to determine whether the initial blood pressure measurement is within a predetermined range of the previous blood pressure measurement.

12. The method of claim 10, wherein the accuracy condition includes determining whether medical condition information of the patient indicates at least one of an arrhythmia and a slow heart rate.

13. The method of claim 12, wherein the wireless blood pressure monitor receives the medical condition information from an electrocardiograph.

14. The method of claim 13, wherein the initial blood pressure measurement is determined not to meet the accuracy condition if the medical condition information indicates a cardiac arrhythmia.

15. The method of claim 10, further comprising controlling the stepwise deflation of the blood pressure cuff to deflate the blood pressure cuff in steps based on the initial blood pressure measurement.

16. The method of claim 15, wherein the blood pressure cuff is deflated in three steps based on the initial blood pressure measurement.

17. The method of claim 15, further comprising controlling the stepwise inflation of the blood pressure cuff to inflate the blood pressure cuff in steps based on the final blood pressure measurement.

18. A method of measuring a blood pressure of a patient in a wireless non-invasive blood pressure monitor, the method comprising:
   continuously inflating a blood pressure cuff of a wireless blood pressure monitor;
   measuring pressure changes in the blood pressure cuff with a pressure sensor during the continuous inflation of the blood pressure cuff;
   determining an initial blood pressure measurement of a patient based on the measured pressure changes;
   determining if the initial blood pressure measurement meets an accuracy condition;
   upon determining that the initial blood pressure measurement does not meet the accuracy condition:
      deflating the blood pressure cuff to two pressure steps based on the initial blood pressure measurement, including:
         determining a systolic pressure estimate and a diastolic pressure estimate based on the initial blood pressure measurement;
         deflating the blood pressure cuff to a first pressure based on the systolic pressure estimate;
         measuring pressure changes in the blood pressure cuff with the pressure sensor while the cuff is maintained at the first pressure to determine a final systolic pressure;
         deflating the blood pressure cuff from the first pressure step-directly to a second pressure based on the diastolic pressure estimate;
         measuring pressure changes in the blood pressure cuff with the pressure sensor while the cuff is maintained at the second pressure to determine a final diastolic pressure; and
      determining a final blood pressure measurement based on the measured pressure changes.

19. The method of claim 18, further comprising determining a maximum required pressure based on the pressure changes measured by the pressure sensor during continuous inflation; and
   controlling inflation of the blood pressure cuff so as not to exceed the maximum required pressure.

* * * * *